United States Patent
Tsoukalis

(12) 
(10) Patent No.: US 7,161,484 B2
(45) Date of Patent: Jan. 9, 2007

(54) SYSTEM FOR MONITORING MEDICAL PARAMETERS

(75) Inventor: Alexandre Tsoukalis, Pallini (GR)

(73) Assignee: Micrel Medical Devices S.A., Pallini (GR)

( * ) Notice: Subject to any disclaimer, the term of this patent is extended or adjusted under 35 U.S.C. 154(b) by 159 days.

(21) Appl. No.: 10/475,042

(22) PCT Filed: Apr. 16, 2002

(86) PCT No.: PCT/EP02/04220

§ 371 (c)(1),
(2), (4) Date: Jul. 12, 2004

(87) PCT Pub. No.: WO02/082984

PCT Pub. Date: Oct. 24, 2002

(65) Prior Publication Data

US 2005/0017864 A1 Jan. 27, 2005

(30) Foreign Application Priority Data

Apr. 17, 2001 (GR) .............................. 20010100200

(51) Int. Cl.
*G08B 1/08* (2006.01)

(52) U.S. Cl. .............................. 340/539.12; 340/539.1; 340/539.17; 340/573.1; 340/825.69

(58) Field of Classification Search ............ 340/573.1, 340/539.1, 539.12, 539.13, 539.17, 539.19, 340/825.49, 825.69; 128/700, 701, 715, 128/903; 600/300, 301, 309, 841
See application file for complete search history.

(56) References Cited

U.S. PATENT DOCUMENTS

| | | | |
|---|---|---|---|
| 3,949,388 A | 4/1976 | Fuller | |
| 4,625,733 A | 12/1986 | Saynajakangas | |
| 5,113,869 A | 5/1992 | Nappholz et al. | |
| 5,152,296 A | 10/1992 | Simons | |
| 5,490,505 A | 2/1996 | Diab et al. | |
| 5,491,474 A | 2/1996 | Suni et al. | |
| 5,544,651 A * | 8/1996 | Wilk | 600/310 |
| 5,720,771 A * | 2/1998 | Snell | 607/60 |
| 6,100,806 A | 8/2000 | Gaukel | |
| 6,198,394 B1 | 3/2001 | Jacobsen et al. | |
| 6,454,708 B1 * | 9/2002 | Ferguson et al. | 600/300 |
| 6,498,652 B1 * | 12/2002 | Varshneya et al. | 356/477 |

* cited by examiner

*Primary Examiner*—Hung Nguyen
(74) *Attorney, Agent, or Firm*—Hahn Loeser & Parks LLP

(57) ABSTRACT

Described is a system for monitoring medical parameters of a being, in particular a human being, comprising medical functional means including at least one sensor section for detecting at least one predetermined medical parameter, a transmitting means for transmitting the medical parameter(s) detected by said sensor section, said transmitting means being adapted to be provided at the being, and a remote serving means for receiving and processing the medical parameter(s) from said transmitting means and providing instructions and/or data on the basis of the processed medical parameters.

27 Claims, 6 Drawing Sheets

```
                    PATIENT WAP
www.xxx.Patient_ppcode
SERVICE XXX
PATIENT NAME:
YOUR CONDITION: AVERAGE
ALARMS: NONE
WARNINGS:-MOVE MOBILE CLOSER TO THE BODY
         -CHANGE BATTERY TO ECG/LOCAL RF
         -TAKE ACTION (E.G. TAKE A PILL)
SENSOR SIGNAL:
ECG: GOOD/LOW BATTERY/LOW
PULSE OXIMETER: AVERAGE/OK/LOW
APNEA:
```

```
                RELATIVE'S WAP
www.xxx.Relative_nncode
SERVICE XXX
PATIENT NAME:
GENERAL CONDITION: AVERAGE
ALARMS: NONE
WARNINGS:NONE
VERDICT:
NO SIGNS OF CONCERN
```

```
              PHYSICIAN WAP
www.xxx.Physician_xxxcode
SERVICE XXX
PATIENT
NAME:
ALARMS: NONE
WARNINGS:NONE
HISTORICAL DATA:
   ·    INCIDENT...
   ·    ...

ANALYTICAL
BPM:
BP:
SO2:
ECG EVENT:
```

FIG. 6

SYSTEM FOR MONITORING MEDICAL PARAMETERS

FIELD OF THE INVENTION

The present invention relates to a system for monitoring medical parameters of a being, in particular a human being.

BACKGROUND OF THE INVENTION

Prior art sensor systems use a local presentation of data which is like "moving hospital at home". Therefore a nurse is visit regularly needed. An alarm is given to a patient who is afraid for everything strange matter of health. A fully healthy person would get stress, when watching his temperature going up and down while he thinks it is stable. On a cardiac disease patient a sudden alarm may be fatal since in some cases he must receive rescue services without prior notice or with a psychologically compiled message.

There are a lot of patents describing two or multi wavelength pulse oximeters, or holter monitors for continuous monitoring of blood gases or cardiac activity, and a few describing a combination of blood pressure ECG and pulse oximeter. ECG monitors and also holter monitors usually use a bundle of cables connected to a thick master cable which is coupled to a monitoring device. This technique cannot be a long time monitoring practice because of the nuisance the cables and pads induce to the user. Prior art holter monitors have at least three self adhesive pads and cables connected to a pocket sized recorder. ECG beepers have a three PIN base to get an ECG when placed on the patient chest and record small portion which is sent by analog telephone to a doctor in case of event. Pulse oximeters have a thumb clip and cable to a pocket sized device showing SO2, PO2, PCO2, PH, HCO3 locally.

EP 0 444 934 A1 discloses a finger ring pressure meter associated to a pulse oximeter for detecting pass/no pass of blood during artery blocking by a pressurized ring. This device is also connected by cables to a monitor and power supply. The pressurizing ring needs power and is bulky so that the whole system is not usable for patients when walking.

U.S. Pat. No. 5,491,474 A discloses pulse rate monitor for training/exercise which takes signals from conductive plastic pads on the patient's chest and transmit them with pulsed RF communication to a wrist pulse rate meter.

The system of U.S. Pat. No. 6,100,806 A uses GPS to track objects or persons.

EP 0 846 440 A discloses a military monitoring system with a bulky jacket type of sensor system.

U.S. Pat. No. 5,113,869 A describes an implantable cardiogram with telemetric capabilities.

There is a need to have a monitoring system as small and with low discomfort to the user as possible, so that it may be worn all the time and not be noticed by other people. There is also a need to have a speedy service to react on any incident, even before it gets serious, and to rescue the patient knowing its location.

SUMMARY OF THE INVENTION

Therefore, the present invention suggests the provision of a system for monitoring medical parameters of a being, in particular a human being, comprising:

medical functional means including at least one sensor section for detecting at least one predetermined medical parameter;

a transmitting means for transmitting the medical parameter(s) detected by said sensor section, said transmitting means being adapted to be provided at the being, and a remote serving means for receiving and processing the medical parameter(s) from said transmitting means and providing instructions and/or data on the basis of the processed medical parameters.

Further advantageous embodiments are defined in the dependent claims.

Accordingly, it is an aim of the present invention to provide a completely mobile medical monitoring system linked with high class decision taking schemes within a distributed service organization, so that all levels of support, e.g. an advice for an action (for example take a pill), a call for examination or a rescue, are taken fast and with all respects of medical, ethical and legal issues.

In particular, an advantage of the present invention is to check if a number of soldiers are living or not, i.e. an operational resource checker in the battlefield, especially in commando operations. Further soldier exercise limits in peace time training can be checked, thus preventing severe accidents. For the first case a finger ring pulse oximeter can be adequate, for the latter case an ECG with possibly a temperature monitor may be added.

The present invention can be called as a tele-medicine service system and is therefore not another home care system, but provides a suitable system for walking and working patients which prevents incidents before they become serious. Preferably, the system of the present invention can use statistics over pre-alarm cases collected from sensors, massive international experience in databases, and live experts in tele/internet-conference or simple consulting, who all have ICU-like (Intensive Care Unit) informations available through the internet, in particular a mobile internet, at any location they may be. It is like every patient carries on his mobile phone a whole ICU including its medical personnel. In alarm cases, a rescue system may be warned, by electronic means.

In the present invention, locally, combined with remote processing power, a state of the art parameter interaction processing and decision taking is assured, allowing also physician interaction, which is legally necessary in some cases, for example to take a pill or change a pump flow rate.

A philosophy of the present invention is "to move the hospital to a service provider" and to send a nurse or ambulance in alarm situations only, while the patient is completely mobile and nobody recognizes that he is being monitored. The sensors themselves do not preferably have display capability, but can be extremely small, while a compiled medical situation can be presented e.g. through a GPRS-WAP page on the patient's phone.

Prior art monitors do not have local sensor signal processing and alarm detection as implemented with the present invention. Due to extremely low power a real time operating system can be achieved by modern electronics and an interrupt driven state machine with the system of the present invention. In contrast thereto, in the prior art all signals are transmitted, preventing them from 24/24 watching patients; when a patient feels a symptom he connects to a transmission device and transmits data. 24/24 monitoring for such system could cost a lot, as e.g. GPRS data content is paid by kilobyte transmitted. However, local signal processing, as provided by the present invention, finds alarm situation and only then transmits data, making its 24/24 use commercially viable.

DESCRIPTION OF THE DRAWINGS

In the following, the present invention will be described in greater detail based on a preferred embodiment with reference to the accompanying drawings, in which:

FIG. 6 shows possible contents of WAP pages for different classes of users like patient, relatives, physicians;

FIG. 7a) which maintains a steady and clear sinusoidal five cycle waveform 71, a transistor 82 to assure the ON period (cf. FIG. 7a), a second input line 86 for the shut down control signal 76, a short circuiting transistor 83 to assure the OFF period 72 (cf. FIG. 7a), an LC tank 81 where L is an antenna coil, a low power trans-conductance operational amplifier with a resistor switch bank (like the ones made by Xicor) for AGC, a microprocessor gain control 83, and a Smith trigger or comparator for a digitized output 84.

DETAILED DESCRIPTION

Figure 1:
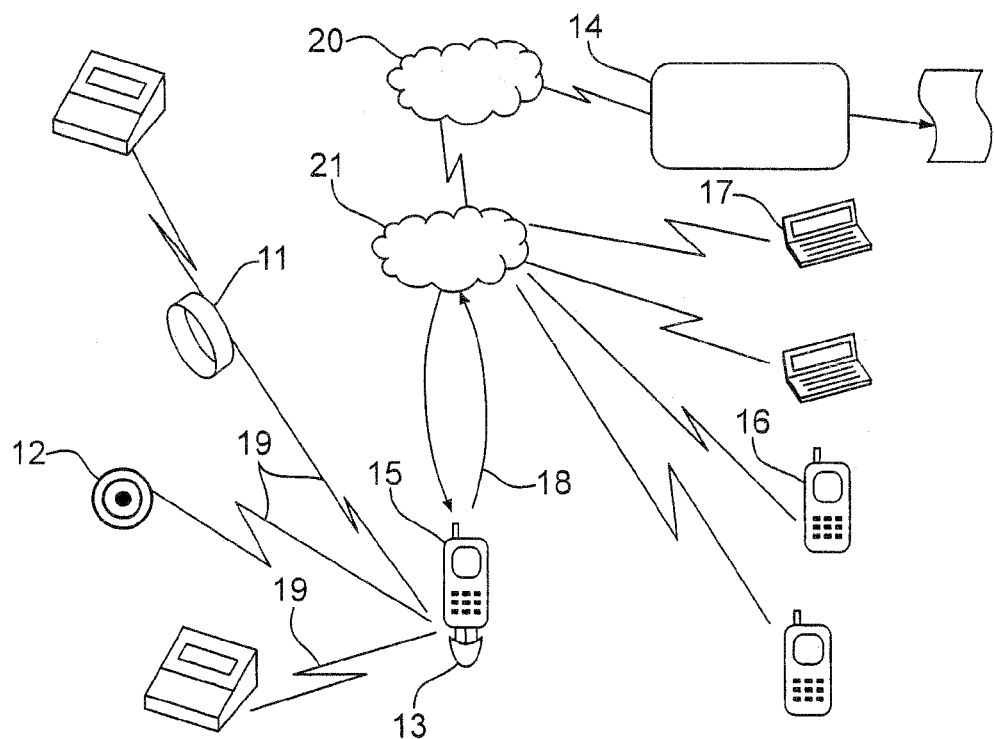
FIG. 1 shows a tele-medicine structure with multiple wireless sensors 11,12, an interface module 13, a mobile internet enabled terminal 15, a service provider computing system 14 with data bases and multiple consultants connected to a further system 16,17.

FIG. 1 shows a preferred embodiment of the whole system which comprises one or more system compatible miniature, self-powered sensors 11,12,41 with local processing capabilities, an interface module 13 which tranceives wirelessly information to/from sensors to/from an internet enabled mobile terminal, and a patient service system 14.

The interface module 13 is an add-on device, permanently connected at the serial port of a mobile terminal 15 and having circuitry for PAN (Personal Area Network) communication 19 with sensors located on the patient's body. It communicates through the mobile terminal with the service system server 14, preferably via GPRS, UMTS, WAP etc., if existing, or SMS or modem communication in case direct internet connection is not possible. Other than internet networks may also be used. It is powered from the mobile's battery, as power consumption shall be in the order of 100 µA when working, i.e. very low power for the terminal battery. The interface module 13 has a server role in local (PAN) information traffic control to and from sensors, using packet switching communication with data correction and anti-collision algorithms. It is connecting also through long distance packet switching network (GPRS/UMTS) to the service system server 14.

Figure 7:
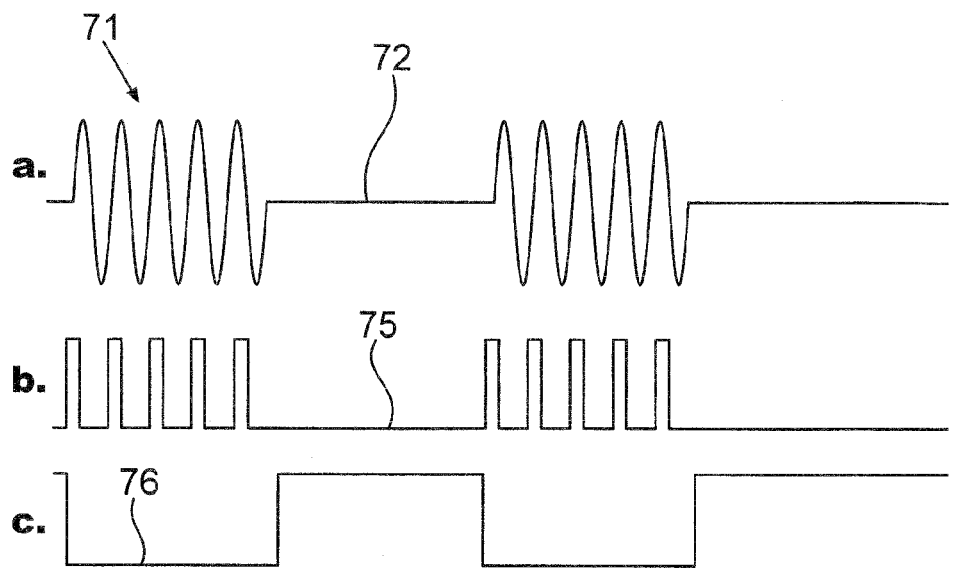
FIG. 7 shows the waveforms of an AM modulated signal emitted which consists of five cycles 71 having a frequency of 125 kHz and five OFF periods 72 (a), an input pulse train signal 75 with one short pulse at every cycle (b), and a shut down control signal 76 (c)
Figure 8:
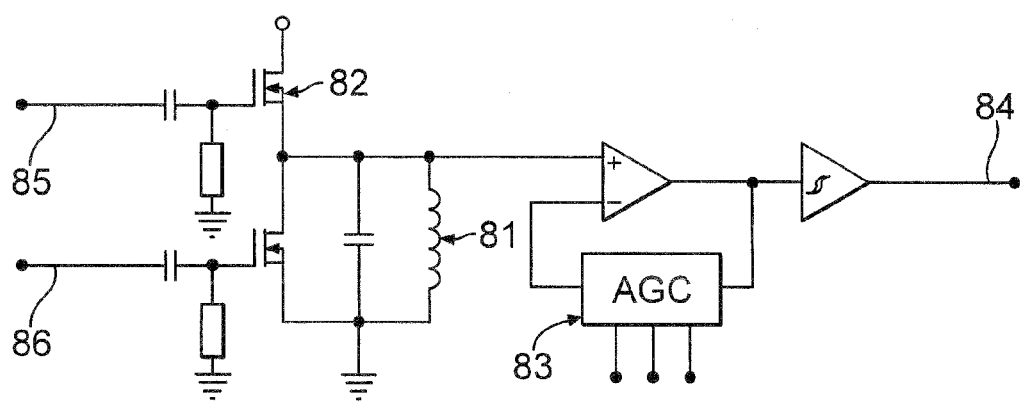
FIG. 8 shows an RF pulse oscillator transceiver comprising a first input line 85 for the pulse train signal 75 of FIG. 7b for an ON period (cf.

In case of RF PAN transmission, a simple pulse oscillator (FIG. 8) is preferably used to send and receive data, with AM (ON/OFF 71/72) modulation (cf. U.S. Pat. Nos. 3,949, 388 A and 4,625,733 A), thus decreasing complexity, size and power consumption as opposed to Bluetooth or other similar technology. A short pulse train signal 75 (FIG. 7b) on the first input line 85 from a microcontroller at 125 KHz sustains the RF ON waveform 71. The short circuiting or stop transistor 83 assures the OFF period 72 (cf. FIG. 7a) due to the shut down control signal 76 (FIG. 7c) on the second input line 86. Low 125 KHz frequency has the advantage of magnetic transmission, which works even under water, useful at shower, in swimming exercise and Nitrogen level detection for divers. This frequency also keeps the microcontroller clock low and, thus, the power consumption; the data to be sent are few and easily sent through this RF frequency. By digitization as shown in FIG. 7, a 125 KHz/10=12.5 KBPS PAN transmission is achieved.

The technology for such low data content information may consume as low as 30 µA used nowadays in a much simpler form for ECG heart beats transmission from a located on-chest-sensor to a watch monitor, for training monitoring and temperature transmission wirelessly. A three dimensional cross ferrite core 27 may expand range to three axes (as described by U.S. Pat. No. 4,625,733 A).

The interface module 13 communicates at agreed intervals with the server 14 to assure good reception from both sides and give a "so far so good" signal. It also handles combination of parameter alarms (for example Beats Per Minute, temperature, arrhythmia and respiration rate), alarming the service center 14 by its own when it gets those parameters from sensors reaching alarm combination levels. The PAN uses a packet switched network communication protocol having error correction and anti-collision algorithms.

The interface module 13 or the mobile terminal 15 itself may in some countries have a GPS location finder, energized when in alarm. In other countries location may be found through phone company antenna triangulation, given as a tool to third party applications. It is a fact that, besides cost weight and size, GPS is problematic at big buildings and generally in cities.

A firmware installed in the interface module 13 handles communication with the mobile terminal 15, and has two basic tasks, namely to let the terminal 15 show uninterruptedly requested WAP pages or to make phone calls, and to tranceive data to and from a remote location, preferably through GPRS or UMTS, in case of class A terminals; for other terminals WAP via GPRS may be used. This is done preferably by AT commands (ETSI standards) and TCP/IP-PPP protocols through a serial port connector of the mobile terminal 15. A mobile phone/internet enabled PDA is another possibility, with bigger size but open application software to third party developers. The parameters with the present invention are not directly presented to the patient, but are first sent together with measurement data to the service center 14 for pre-processing with more complete algorithms and possibly human interaction, and act according to patient contract, doctor needs and legal, ethical and medical issues. Then the WAP page is renewed, or a SMS message or a phone call is sent back to inform the patient accordingly.

In case an RFID implantable tranceiver sensor is used, an RFID base station is built on a body surface place close to it, communicating with a different RF frequency from that of PAN, still used for communication from this device to the interface module 13.

The system compatible sensors 11, 12, 41 have integrated a source of energy if they are active, or RFID power if passive. They also have a PAN circuitry, which in case of RF transmission may include a pulse oscillator described above, an antenna coil, and a low power microprocessor able to locally process data and extract alarm warning. In such a case, they send the alarm and no loss compressed data enough to judge upon the case to the server. The intervals of measurement and alarm limits are received from the server through its initial connection, or the service center 14 may issue a command for continuous monitoring in some extreme cases. There are also pre-alarms which may be issued without sending all data. The interface module 13 interrogates, at an agreed rate the sensors to see a sensor ID code plus battery condition and reception quality as well as possible problems. The sensors 11, 12, 41 may request to send message immediately after warning detection. High Density Packaging (HDP) such as MCM (Multi Chip Module), Flip-Chip, or ASIC is used for miniaturization of the sensors.

Figure 2A:
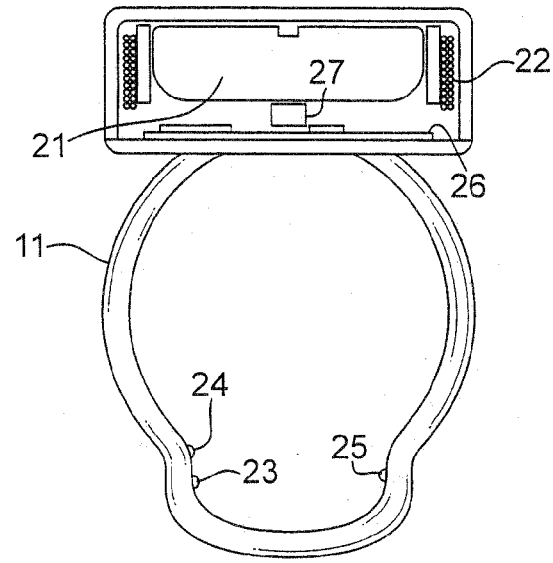
FIGS. 2a and b shows a system compatible finger ring type pulse oximeter sensor 11 comprising a button cell battery 21, a coil RF antenna 22, red and infrared LEDs 23,24, a photo-detector 25, a circuit with a microcontroller, regulators, an analog circuitry and a RF tranceiver connection to a microcontroller 26 for wireless transmission to the interface module 13.
Figure 2B:
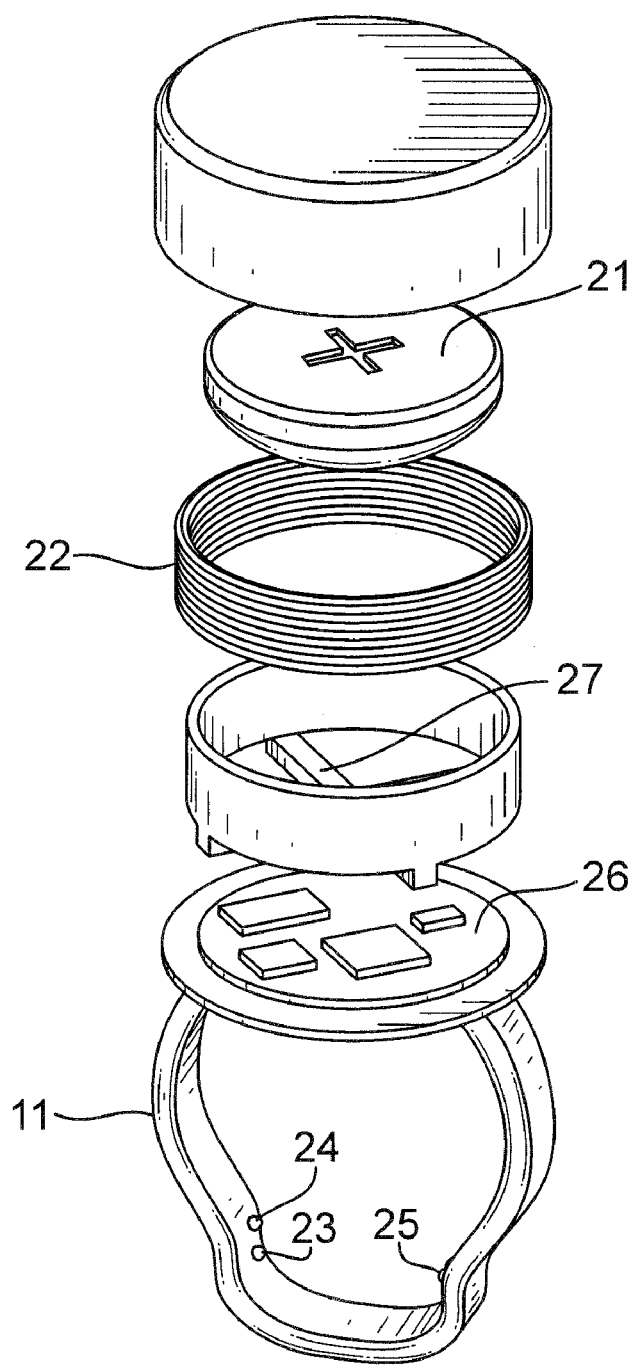
Figure 3:
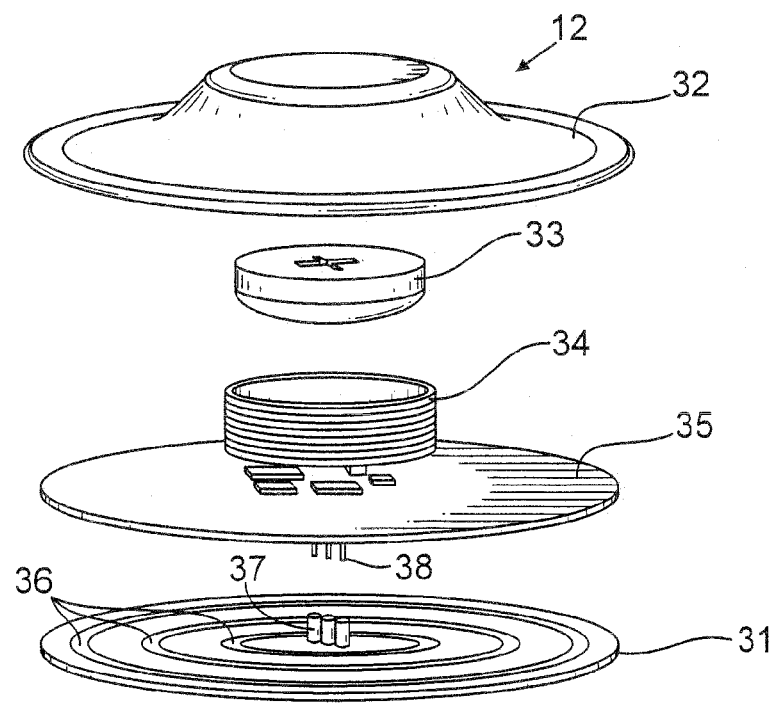
FIG. 3 shows a system compatible sensor ECG monitor 12, comprising a Laplacian electrode consumable ECG pad 31 with a connector 37, a plastic top 32, comprising a connector 38 to the pad, a button cell battery 33, a coil RF antenna 34, a circuit 35 with a microcontroller, regulators, an analog circuitry and a RF tranceiver connection to the microcontroller for wireless transmission to the interface module 13.

One type of sensor is a finger ring pulse oximeter 11 shown in FIGS. 2a and b, which measures blood gas parameters, using two or more LEDs and one detector at opposite sides of the finger. The optical line is situated under the finger bone, to enhance signal quality. So the finger ring narrows at the bottom to slightly shape in a more elongated form flesh underneath the bone. This helps also fix the finger ring more tightly over the bone, with the elongation helping so that it cannot move out or rotate, while artifacts are reduced. At both outer sides of the finger ring preferably flexible curtains are placed to block external light. The finger ring is provided in form of an elastic or hinge opening to be removed in/out the finger, so that the patient can change the position to different finger from time to time.

$SO_2$ is calculated by a known derivative value of the AC component of the waveform measurement of the Ratio of Ratios, using linear regression algorithm. This gives good results with signals having same noise in both waveforms, but a wrong result when different noise at each signal is present. An algorithm comprising a kind of adaptive filter including correlator of two signals has been developed wherein normally both red and IR signals go up or down together. U.S. Pat. No. 5,490,505 A shows a correlation of a two signals algorithm, whereas the algorithm used in the present embodiment of the invention is of a different kind which does not filter at all if signals change essentially at the same direction and same proportion. The same algorithm handles artifact rejection.

A pulse oximeter may also detect variations of pressure by $SO_2$ blood pulse waveform, as demonstrated by GB 2 076 963 A1. It measures the variation of pressure plus blood parameters ($SO_2$, $PO_2$, $PCO_2$, PH, $HCO_3$,$N_2$) or metabolic (for example glucose) parameters and detects if a limit is reached, to output a warning. For multiple parameters, more LEDs are used as taught by U.S. Pat. No. 5,630,413 A.

A wrist or any other type of a system compatible absolute pressure meter exactly measures several times per day a pressure level which is also sent by the same way or by keystrokes on the mobile terminal 15 to the service center 14. There, all information is reconstructed, and absolute pressure for every moment is calculated. In case of a relative overpressure detection, the patient is warned by his mobile 15 to make a new and exact pressure measurement. In case of pressure limit reached, data are analyzed taken account of his medical file, and then, he gets written WAP or SMS instructions to get a pill, which may prevent implications and save his life.

The provision of an implantable RFID powered passive telemetry blood pressure sensor placed in the blood flow or inside heart is possible with the present architecture. It may comprise a capacitive pressure sensor, a analog circuit, a microcontroller or an ASIC, and a RFID chip which provides power from RF reception, and passively sends data to the extra-corporeal interface module 13. All is packaged in an elongated ultra-small capsule, possibly using MCM (Multi Chip Module) or Flip Chip, ASIC packaging and miniaturization techniques. The sensor may be covered with PARYLENE which reduces the problem of tissue build up.

The relative pressure system has the advantage of safer use at not severe situations. Each one of these pressure measurement systems, implantable or not, but implemented with the proposed technology, presents a total solution to the overpressure problem.

The finger ring pulse oximeter is a simple finger ring looking device which alone with the telemetry system (i.e. interface module 13, mobile phone 15 with application software, service center software, service provider organization/human resources) may be useful for pneumonological disease cases or elderly people alone at home. It gives SO2 or/and all other above mentioned five possible parameters, beats per minute, peripheral blood temperature, detects arrhythmia from blood pulses and relative pressure. This is most of what is needed for these categories of people.

An RFID technology is developed for passive (without battery) radio reception of ID codes from not powered RFID tags placed on several places; this is e.g. the way animals are counted today.

Passive telemetry works like this: You emit at say 125 KHz (other frequencies are also possible in today's RFID chips) from a base station, and have at a short distance an RFID tag with a coil and capacitor (LC circuit) tuned at same frequency. If the capacitor/antenna is short-circuited with a simple transistor for a few cycles, the emitter receives different back scattered intensity from the antenna and so distinguishes bits of data received. As it is apparent, power for transmission is not used, but the antenna is short-circuited; this is passive telemetry. RFID passive telemetry has a short range, a few centimeters, depending on the power of the transmitter and a two (receiver/transmitter) antennas design. Passive telemetry (RFID) systems convert RF energy to DC voltage, then charge a capacitor, for powering internal circuits. A few hundreds of microamperes at 3V may be sucked from this system, which is more than enough to power a microcontroller and associated circuits.

There is at least one RFID single chip (from ATMEL) doing both reception and passive transmission, connectable to a microcontroller. This chip in form of an unpacked chip has very small dimensions good for the application in the system of the present invention. RFID technology is mandatory for implantable sensors, as a battery is not needed to be implanted, and so the sensor is small and can be placed almost everywhere.

In the non-implantable sensors, a battery is usually provided, so that a pulse oscillator can be powered with local power. Thus, the powered tranceiver placed at the interface module 13 does not have to emit all the time and consume energy from the mobile terminal 15.

State of the art microcontrollers (like MSP430 from Texas Instruments) with an integrated A/D converter use extremely low power consumption. For the present system, a real time operating system, event/interrupt driven, may consume less than 40 µA. These microcontrollers have an internal architecture which make fast and easy wave digital filtering directly on 16 bit numbers. Low power DSPs are also another alternative. New operational amplifiers are working on 5–10 µA at 3V power consumption. In the architecture of the system of the present invention, only components are turned on which are needed at that time, whereas all the others being shut down.

In the present system, signals are locally processed, and first alarm conditions (for instance arrhythmia types) are extracted, when needed, due to such low power. Such a low power is generated by a button cell battery. It also makes the provision of a completely passive implantable ECG monitor (getting power from the RFID chip)—and implantable in the blood flow pressure sensor—possible, as power consumed from an ECG or pressure sensor is extremely low, since it has no LEDs or other active devices, other than processing.

Figure 5:
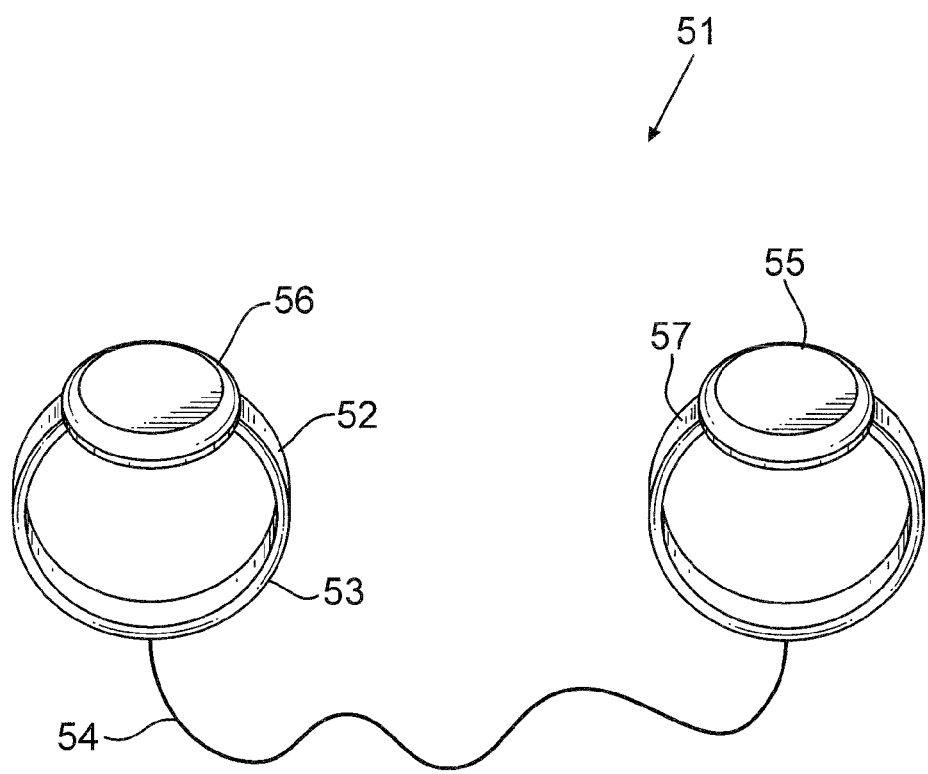
FIG. 5 shows a system compatible wrist pressure meter/ECG monitor 51 comprising a pressure inflatable measuring device 52, a first wrist belt ECG electrode 53, a wire connection 54 to a second wrist belt/ECG electrode 57, a battery 55, a coil RF antenna 56, a circuit with microcontroller, regulators, a analog circuitry and an RF tranceiver connection to the microcontroller for wireless transmission to other sensors.

The sensor ECG monitor of the present invention does not use cables if a single self adhesive pad 12 is used. Alternatively, two wrist belts linked by a cable provided from one hand to the other hand underneath clothes are used (FIG. 5). The single pad sensor uses two or three circular concentric circuit detector electrodes 36, as described in the literature as Laplacian electrode (cf. Bin He and Richard J. Cohen *IEEE Transactions on Biomedical Engineering* Vol. 39, No. 11, November 1992). The electrodes may also be a part only of the cycle or locally distributed self adhesive pads with flat cable interconnection. Added is a plastic or elastic top 32 to the consumable pad, which comprises a system compatible electronic architecture according to the present invention, and which gets body signals from the pad underneath by a connector, while the total system looks like a normal pad of prior art's ECG pads.

The ECG pad monitor 12 may also comprise on the consumable 31 IR and red LEDs, an optic detector forming a pulse oximeter, and a temperature sensor, located in the center of the pad with metallized circles of Laplacian electrodes around, for reflective type pulse oximetry and temperature monitoring.

The system compatible architecture described above has a microcontroller which filters digitally the waveform, then extracts a number of cardiac disfunction parameters like arrhythmia types, and digitally processes the filtered waveform. Algorithms for detection of arrhythmia are relatively simple, (cf. Abenstein J. P. 1978 *Algorithms for real-time ambulatory ECG monitoring Biomed. Sci. Instrum.* 14:73–79). For ischemia detection, more elaborated algorithms are needed, using preferably neural networks (cf. C. Papaloukas, *Proceedings of the fourth International Conference on Neural Networks and Expert Systems In Medicine and Healthcare* 2001). Ischemia detection or vector ECG (12 pole) need more than one ECG sensor 32 to get signals from different parts of the body, all referenced to ground. Packets of data sent (PAN) to and from said interface module 13 are synchronized by a reference real time clock sent together with a poling packet. The sensors, at their turn, send start of waveform real time reference together with packet sent. So, the interface module 13 may reconstruct exact relative timing of each waveform for using the algorithm, and, thus, multi-waveform analysis is done. The packet transmission rate (12.5 KHz or more) is much higher than the measuring rate (500 Hz), as many sensors may be in the network without collision. The emission through PAN is done upon event recognition, and then data around event point are sent, or after demand from the service center.

The dual wrist belt interconnecting cable system of FIG. 5 may include all the above mentioned electronics like a watch in one hand and be integrated/combined with a wrist pressure meter in one instrument.

Figure 4:
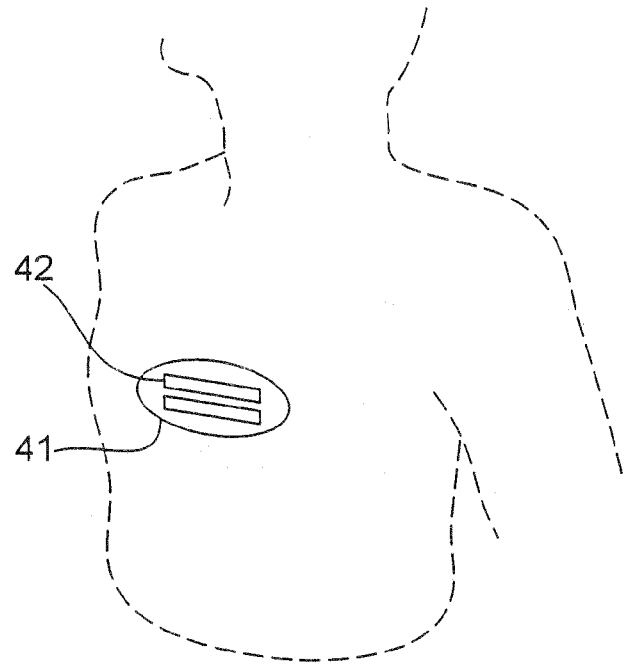
FIG. 4 shows a chest belt type system compatible respiration monitor 41 comprising an inductive plethysmograph elongation sensor or strain gauge 42, a button cell battery, a temperature sensor, a coil RF antenna, a circuit with microcontroller, regulators, an analog circuitry and an RF tranceiver connection to the microcontroller for wireless transmission to the interface module.

A breath detector belt system, shown in FIG. 4 and using one or more strain gauge sensors or inductive plethysmographs as described in U.S. Pat. Nos. 4,308,872 A, 531,968 A and 6,047,203 A, compatible with the system, gives breaths per minute and a cardiac output. It sends breaths per minute, if a single sensor or full data in case of multiple sensors is used, to the interface module 13 which combines them or with other sensor parameters to issue an alarm or pre-alarm.

The service provider 14 is the one who has the contact with patients, their doctors and overall responsibility of quality of service. Quality of service has many categories:

How fast is the rescue in case of an incident at a given location area?

How good is the discrimination of an incident from the normal situation (no false alarms)?

Which experts are available and how fast in case of an incident?

Give a choice of experts to the patient, depending on a scaled price, including his personal doctor.

How severity of incident is categorized?

How the presentation of data to different categories of interest is done according to their needs?

How much a patient's personal doctor is respected, how is he entering into play in case of incident, and how comfortable a patient is feeling with this scheme?

There shall be as many application differences as the number of service providers. The system provided on the internet 20 means that a proven good provider using the present invention, based in one country, may take decisions for patients in another country, needing only a good rescue system based there.

Payment for the service may be on a monthly service basis, and some insurance companies may offer it to their clients for a special discount.

The service provider 14 may not be a single entity; data processing and local rescue/marketing/customer service may comprise an information chain and be business to business related, and even be at different countries. The service center or a processing unit linked to it shall re-process transmitted data from the mobile terminal 15 with more complete algorithms and effect automatic action, using a data base including the patient contract, the medical file, the medical practice, the local ethics, and, if needed, advice from paramedics personnel watching data. Even a conference is possible from doctors defined in the patient's contract.

Besides the alarms sent by sensors, one or more pre-alarm levels may also be sent, building a statistical event database, which are very valuable in determining therapy by doctors. An alarm needs some action like a call, a warning and/or a rescue, while pre-alarms are more transparent and provides a health qualification information up-dating e.g. WAP pages. A certain frequency of pre-alarms may, combined to other parameters measured, or in the patient's database, induce an alarm issued directly from the service center 14. An alarm may send data together with its code, while a pre-alarm may not, depending on local data price list and customer's contract/payments.

Display data not from sensors directly but only after massive remote processing and though medical, legal, ethical, and company policy decision flowcharts, is another topic of the present invention.

The patient contract is an essential part of the system as it describes the patient's preferred language, alarm limits of the sensors or combination of them, what to show to whom (like relatives and patient himself), special non standard religious or ethical aspects guiding reaction to alarms as well as medical doctor preferences and linked WAP addresses and/or telephone numbers, the level of rescue according to the financial situation, for example helicopter for one, ambulance for the other, teleconference of professors of medicine in one case or family doctor in the other case etc. The patient contract contains also his medical file (illness history) or has link to another location to find it.

The invention claimed is:

1. A system for monitoring medical parameters of a being, in particular a human being, comprising:
    medical functional means including at least one sensor section for detecting at least one predetermined medical parameter;
    a transmitting means for transmitting the at least one predetermined medical parameter detected by said at least one sensor section, said transmitting means being adapted to be provided at the being;
    a remote serving means for receiving and processing the at least one predetermined medical parameter from said transmitting means and providing at least one of instructions and data on the basis of the processed medical parameter, wherein
    said medical functional means is adapted to create pre-alarm signals providing health qualification information, and wherein
    said medical functional means is adapted to transmit said pre-alarm signals, and wherein
    said remote serving means is adapted to process said pre-alarm signals.

2. The system according to claim 1,
    wherein said remote serving means is adapted to give an alarm in case of a predetermined frequency of said pre-alarm signals.

3. The system according to claim 1, wherein said transmitting means is connected with said remote serving means via a network wireless connection.

4. The system according to claim 1, further comprising a receiving means for receiving the at least one of instructions and data from said remote serving means, said receiving means being adapted to be provided at the being.

5. The system according to claim 4, further comprising a communication device, wherein at least parts of said transmitting means and said receiving means form said communication device.

6. The system according to claim 5, wherein said transmitting means comprises an interface means connected with said communication device for receiving the at least one medical parameter from said medical functional means.

7. The system according to claim 6, wherein said receiving means comprises an interface means connected with said communication device for transmitting the at least one of instructions and data received from remote serving means to said medical functional means.

8. The system according to claim 4, wherein said receiving means is connected with said remote serving means via a network wireless connection.

9. The system according to claim 4, wherein said medical functional means includes a receiving section for wireless connection with said receiving means.

10. The system according to claim 1, wherein said medical functional means includes a transmitting section for wireless connection with said transmitting means.

11. The system according to claim 1, wherein said medical functional means includes a power source.

12. The system according to at least claim 1, wherein said medical functional means includes a passive telemetry power section for receiving external remote power.

13. The system according to claim 1, wherein said at least one sensor section comprises at least one of a blood gas pulse oximeter analyzer and metabolic parameters pulse oximeter analyzer.

14. The system according to claim 13, wherein said pulse oximeter analyzer locally processes and measures at least one of $SO_2$, $PO_2$, $PCO_2$, $PH$, $HCO_3$, $N_2$ with ill least one of multi wavelength measurements and preferably multivariate analysis.

15. The system according to claim 13, wherein said pulse oximeter analyzer extracts at least one of heart arrhythmia information, beats per minute and relative blood pressure.

16. The system according to claim 1, wherein said at least one sensor section comprises at least one ECG monitor, in the form of two connecting parts, a Laplacian Electrode consumable pad, comprising two or more concentric cyclic electrodes having a shape of at least a portion of a cycle connecting on top with non consumable self-powered electronic part~, comprising analog, digital, and PAN parts.

17. The system according to claim 16, wherein said digital part filters and locally analyses ECG waveforms, extracting at least one of medical useful information and symptoms, by at least one of standard signal processing, fuzzy logic and neural networks type, detecting known cardiac abnormalities, including at least one of arrhythmia types, early detection of ischemia and deterioration of ischemia.

18. The system according to claim 16, comprising a plurality of ECG monitors, wherein the corresponding waveforms are synchronized by real time clock reference using digital PAN, wherein a multi-waveform ECG is reconstructed and used for at least one of vector and other analysis, at least part of which is done remotely by said remote serving means.

19. The system according to claim 1, wherein said at least one sensor section comprises an implantable ECG detector combined with a temperature sensor, getting power from external RFID signals and passively transmitting back at least one of signals and symptoms information processed on site, having internal wire connection to parts of the body.

20. The system according to claim 1, wherein said sensor section comprises a watch inflatable type pressure sensor, which has a wire connected wrist belt ECG electrode for at least one hand.

21. The system according to claim 1, wherein said at least one sensor section comprises an implantable passive telemetry pressure sensor.

22. The system according to claim 1, wherein said at least one sensor section comprises a respiration sensor of inductive plethysmograph type for detecting cardiac output.

23. The system according to claim 1, further comprising:
   a display means for displaying the at least one of instructions and data provided by said remote serving means.

24. The system according to claim 23, said communication device comprising said display means.

25. The system according to claim 1, wherein said medical functional means comprises an infusion pump, being adjusted so as to be controlled by the at least one of instructions and data provided by said remote serving means.

26. The system according to claim 13, wherein the at least one sensor section comprises a self contained finger ring with a light path to be located under a finger bone, the ring shape disabling rotation, and having light blocking flexible curtains at both sides.

27. The system according to claim 16, wherein the consumable pad is combined with at least one of a reflective type pulse oximeter, strain gauge for breath detection, and temperature sensor.

* * * * *